(12) United States Patent
Lee et al.

(10) Patent No.: US 9,364,190 B2
(45) Date of Patent: Jun. 14, 2016

(54) COMPACT MAMMOGRAPH AND ASSOCIATED MAMMOGRAPHY PROCESS

(75) Inventors: Susanne Madeline Lee, Cohoes, NY (US); Aurelie Boudier, Bois d'Arcy (FR); Serge Louis Wilfrid Muller, Guyancourt (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 177 days.

(21) Appl. No.: 13/300,083

(22) Filed: Nov. 18, 2011

(65) Prior Publication Data

US 2012/0134465 A1 May 31, 2012

(30) Foreign Application Priority Data

Nov. 26, 2010 (FR) ..................................... 10 59786

(51) Int. Cl.
*A61B 6/00* (2006.01)
*B82Y 10/00* (2011.01)
*G21K 1/06* (2006.01)
*H01J 35/06* (2006.01)
*A61B 6/08* (2006.01)

(52) U.S. Cl.
CPC .................. *A61B 6/482* (2013.01); *A61B 6/502* (2013.01); *A61B 6/588* (2013.01); *B82Y 10/00* (2013.01); *G21K 1/06* (2013.01); *H01J 35/06* (2013.01); *A61B 6/08* (2013.01); *A61B 6/4021* (2013.01); *G21K 2201/061* (2013.01); *G21K 2201/064* (2013.01); *H01J 2235/068* (2013.01)

(58) Field of Classification Search
CPC ........................... H01J 2235/068; A61B 6/502

USPC ............................................................ 378/37
See application file for complete search history.

(56) References Cited

U.S. PATENT DOCUMENTS

| 6,140,649 | A * | 10/2000 | Lonn ........................ 250/363.04 |
| 6,292,531 | B1 * | 9/2001 | Hsieh ............................... 378/37 |
| 6,483,891 | B1 * | 11/2002 | Lazarev et al. ................... 378/37 |
| 6,674,837 | B1 * | 1/2004 | Taskar et al. ................... 378/122 |
| 7,092,482 | B2 * | 8/2006 | Besson ............................ 378/37 |
| 7,103,138 | B2 * | 9/2006 | Pelc et al. ......................... 378/9 |
| 7,366,374 | B1 * | 4/2008 | Lee et al. ......................... 385/31 |
| 7,885,378 | B2 * | 2/2011 | Kopans et al. ................... 378/21 |
| 2005/0078797 | A1 * | 4/2005 | Danielsson et al. .......... 378/145 |

(Continued)

FOREIGN PATENT DOCUMENTS

| JP | 11275488 A | 10/1999 |
| JP | 11285488 A | 10/1999 |

(Continued)

OTHER PUBLICATIONS

French Search Report for FR Application No. 1059786 filed on Nov. 26, 2010 issued on Jul. 4, 2011.

(Continued)

*Primary Examiner* — David J Makiya
*Assistant Examiner* — Dani Fox
(74) *Attorney, Agent, or Firm* — GE Global Patent Organization; Marc A. Vivenzio

(57) ABSTRACT

A mammograph is provided. The mammograph includes a source of X-rays; a detector of X-rays, the source being configured to emit at least one beam of X-rays to the detector; and an optic control device configured to control the direction of X-rays emitted by the source such that the X-rays emitted by the source are substantially parallel to one another.

11 Claims, 6 Drawing Sheets

(56) References Cited

U.S. PATENT DOCUMENTS

| | | |
|---|---|---|
| 2006/0018429 A1 | 1/2006 | Hoghoj et al. |
| 2008/0247509 A1* | 10/2008 | Kashiwagi ............... 378/54 |
| 2009/0022264 A1* | 1/2009 | Zhou et al. ............... 378/5 |
| 2009/0147922 A1* | 6/2009 | Hopkins et al. ........... 378/140 |
| 2009/0232271 A1* | 9/2009 | Sendai ...................... 378/8 |
| 2010/0020925 A1* | 1/2010 | Moore et al. .............. 378/25 |

FOREIGN PATENT DOCUMENTS

| | | |
|---|---|---|
| JP | 2007216022 A | 8/2007 |
| JP | 2008068032 A | 3/2008 |
| JP | 2008237631 A | 10/2008 |
| JP | 2008307236 A | 12/2008 |
| JP | 2010167129 A | 8/2010 |
| WO | 9953823 A2 | 10/1999 |
| WO | 03073939 A1 | 9/2003 |
| WO | 2007050025 A2 | 5/2007 |
| WO | 2009012453 A | 1/2009 |

OTHER PUBLICATIONS

Erik Fredenberf, Bjorn Cederstrom, mats Danielsson, Mats Lundqvist, Magnus Aslund, and Magnus Hemmendorff: A photon-counting detector for dual-energy breast tomosynthesis, SPIE, PO Box 10 Bellingham, Washington 98227-0010, The United States of America, Feb. 9, 2009, XP040494523, DOI: 10.1117/12.813037.

Unofficial translation of Japanese Office Action from corresponding JP Application No. 2011-255658 dated Aug. 25, 2015.

Unofficial English Translation of Japanese Office Action and Search Report issued in connection with corresponding JP Application No. 2011255658 on Apr. 6, 2016.

* cited by examiner

COMPACT MAMMOGRAPH AND ASSOCIATED MAMMOGRAPHY PROCESS

BACKGROUND OF THE INVENTION

1. Field of the Invention

Embodiments of the present invention relate to a mammograph and a mammography process.

2. Description of the Prior Art

Mammography is a radiography technique for studying the breast of a patient for clinical and/or interventional purposes. It can especially detect early-stage breast cancer in a patient, and/or repair lesions leading up to surgical intervention.

FIG. 1 schematically illustrates a mammograph 50 in an embodiment known from the prior art. The mammograph 50 comprises a source 51 of X-rays capable of emitting a beam 52 of X-rays to a frame 53 comprising a lower block 54, on which the breast 56 of a patient rests, and an upper plate 55, a so-called compression pad. The upper plate 55 is mobile in vertical translation so as to compress the breast 56 of the patient against the lower block 54. The lower block 54 also comprises a detector 57, whereof the detection surface 58 is turned to the beam 52, directly below the breast 56. The beam 52 of X-rays emitted by the source 51 reaches the breast 56 of the patient, and the detector 57 then captures the X-rays transmitted by the breast 56 to take a mammographic image. As can be seen, the beam 52 of X-rays has a substantially conical form, generally rectangular in cross-section, whereof the apex is an emission focal spot located at the level of the source 51.

As is evident, for an image to be taken of the entire breast 56 of the patient it is necessary to have a distance between the detector 57 and the source 51 greater than a certain value to avoid parts of the breast being omitted in the image. Yet, the compactness of the mammograph 50 is especially characterised by the distance between the source 51 and the detector 57. As a consequence, prior art devices are not very compact.

The effect of bringing the source 51 closer to the detector 57 in the prior art mammographs would be to omit part of the breast 56 in the image. Also, X-rays are generally emitted from a metallic anode being impacted at an emission focal spot by a beam of electrons emitted by a cathode.

Increasing the size of the emission focal spot involves boosting the quantity of X-rays to be emitted throughout exposure of the detector to the rays. This is translated by a shorter acquisition time for a given quantity of X-rays reaching the detector, and therefore less risk of the breast moving during image acquisition, and ultimately improvement in the final image quality, which is interesting for the practitioner.

But a large-sized emission focal spot, associated with a small distance between the detector and the source, causes degradation of the image quality by the appearance of blurring in the prior art mammographs, apart from truncation of the breast in the image previously mentioned. In particular, visibility of some zones of interest, such as micro-calcifications, is degraded in the image. Prior art mammographs cannot therefore simultaneously reconcile compactness and image quality.

Also, as shown in FIG. 2, prior art mammographs require the use of a protective cover 59 for pushing back the head of the patient out of the image-taking zone, between the source and the detector. Indeed, in these mammographs the source is placed above or at the level of the head of the patient, along a vertical axis.

Due to the position of the patient under compression or to the pressure exerted by the protective cover on the patient, the breast of the patient tends to also be pushed back from the imaging zone, the disadvantage of which is to reduce the portion of the breast viewed by the mammograph, as well as creating a source of discomfort for the patient.

Embodiments of the present invention dispense with the above disadvantages

BRIEF SUMMARY OF THE INVENTION

According to an embodiment of the present invention, a mammograph is provided. The mammograph includes a source of X-rays; a detector of X-rays, the source being configured to emit at least one beam of X-rays to the detector; and an optic control device configured to control the direction of X-rays emitted by the source such that the X-rays emitted by the source are substantially parallel to one another.

According to an alternate embodiment of the present invention, a method of mammography using a mammograph is provided. The mammograph includes: a source of X-rays; a detector of X-rays, the source being configured to emit at least one beam of X-rays to the detector; and an optic control device configured to control the direction of X-rays emitted by the source such that the X-rays emitted by the source are substantially parallel to one another. The method includes emitting at least one beam of X-rays from the source to the detector, the X-rays of the beam being substantially parallel to one another.

BRIEF DESCRIPTION OF THE DRAWINGS

The accompanying drawings, which are incorporated, in and, constitute a part of the specification, illustrate one or more embodiments and, together with the description, explain these embodiments. In the drawings.

DETAILED DESCRIPTION OF THE INVENTION

Figure 1:
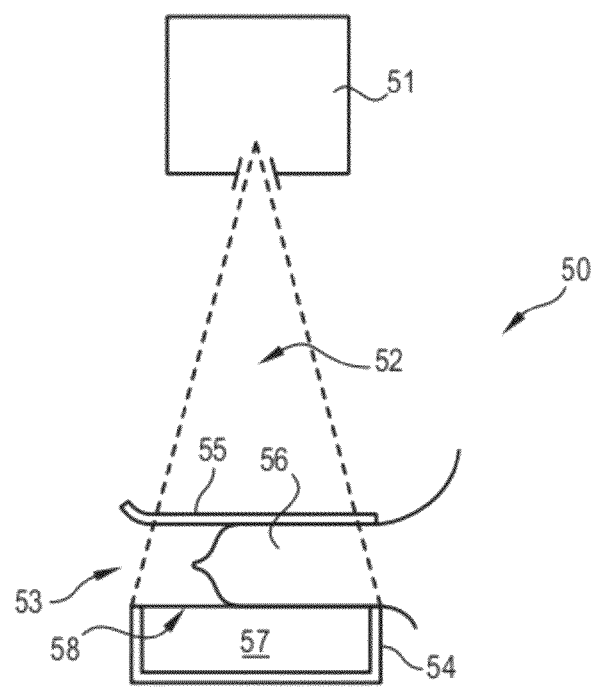
FIG. 1 is a schematic representation of a mammograph according to the prior art.
Figure 2:
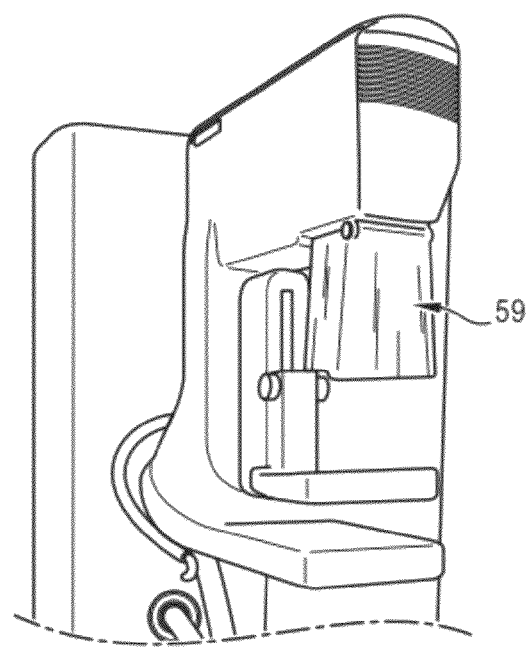
FIG. 2 is a view of a mammograph according to the prior art.
Figure 3:
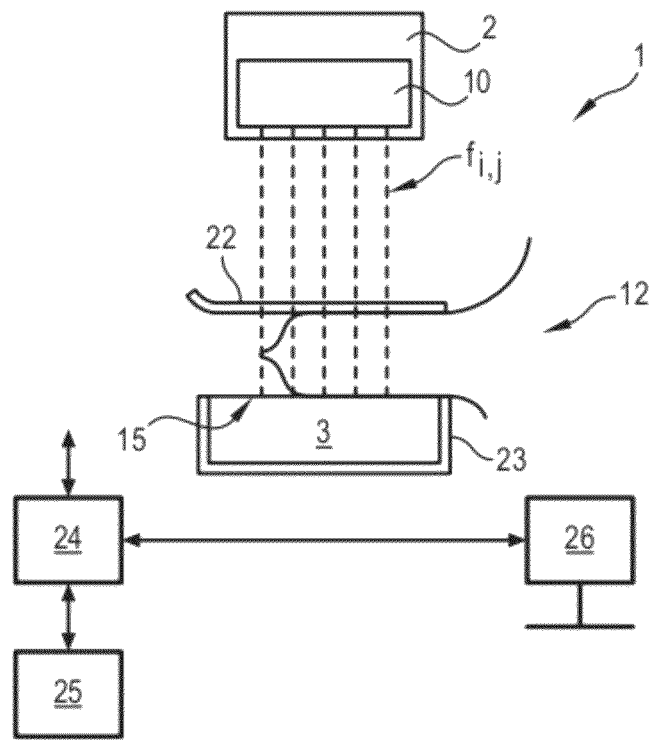
FIG. 3 is a schematic representation of a mammograph according to an exemplary embodiment of the present invention.

FIG. 3 is a schematic representation of a mammograph 1 according to an exemplary embodiment of the present invention. The mammograph 1 comprises a source 2 of X-rays and a detector 3 of X-rays. The source 2 of X-rays is capable of emitting at least one beam $f_{i,j}$ of X-rays to the detector 3, for conducting mammography of a patient 12.

The mammograph 1 comprises an upper plate 22, a so-called compression pad, and a lower block 23. The upper plate 22 is mobile in vertical translation to compress the breast of the patient 12 against the lower block 23. Alternatively, or in addition, it is the lower block which is mobile for compressing the breast.

The detector 3 comprises a detection surface 15 turned to the beam $f_{i,j}$, under the breast of the patient 12. The detector 3 is, for example, an image sensor with semi-conductors comprising, for example, caesium iodide phosphor (scintillater) on a matrix of transistor/photodiode of amorphous silicon. Other adequate detectors include a CCD sensor. These types of detector are given by way of non-limiting examples.

The beam $f_{i,j}$ of X-rays emitted by the source 2 encounters the breast of the patient 12, the detector 3 sensing the X-rays transmitted by the breast to take a mammographic image. An anti-diffusing grid can be provided between the source 2 and the detector 3, comprising absorption blades ("septa") opaque to radiation, which enables the unwanted rays diffused by the breast of the patient 12 to be filtered. Alternatively, or in addition, collimation between the source 2 and the detector 3 can be provided.

In conventional terms, the mammograph 1 may comprise a control unit 24, a storage unit 25 and a display unit 26. The control unit 24 controls acquisition by fixing several emission parameters of X-rays by the source 2. The control unit 24 also controls displacement of the source 2 and/or of the detector 3, as well as their relative positions. The control unit 24 is typically a microcomputer and/or a processor.

The storage unit 25 is connected to the control unit 24 to record parameters and acquired images. It is possible to ensure that the storage unit 25 is located inside the control unit 24 or outside the control unit 24. The storage unit 25 can be formed by a hard drive or SSD, or any other removable and rewritable storage means (USB keys, memory cards, etc.). The storage unit 25 can be ROM/RAM memory of the control unit 24, a USB key, a memory card, memory of a central server, etc.

The display unit 26 is connected to the control unit 24 for displaying the acquired images and/or information on the acquisition control parameters. The display unit 26 can be for example a computer screen, a monitor a flat screen, a plasma screen or any other type of display device of known type. Such a display unit 26 enables a practitioner to view and control the acquisition of images by the mammograph. The mammograph also conventionally comprises means for interaction by a practitioner, of keyboard type.

It is understood that functional clipping of the different control, display and storage units which have just been described can be different according to embodiments and needs.

The mammograph 1 also comprises an optic control device 10, configured to control the direction of X-rays emitted by the source 2 to the detector 3, in such a way that said X-rays emitted by the source 2 to the detector 3 are substantially parallel to one another.

Figure 4:
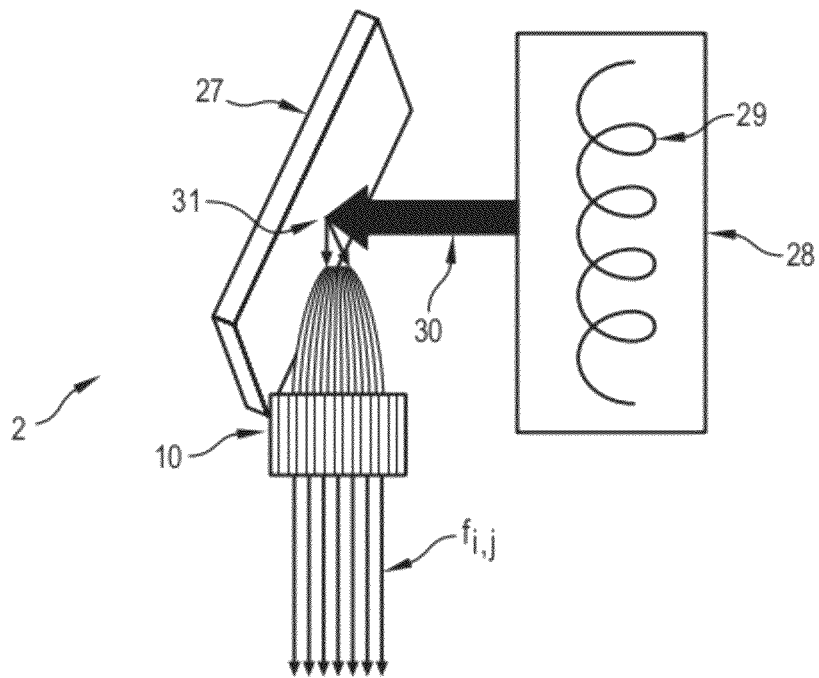
FIG. 4 is a schematic representation of elements of a source of X-rays according to an exemplary embodiment of the present invention.

FIG. 4 schematically illustrates an exemplary embodiment of the source 2 of X-rays and of the optic device 10.

In general, the source 2 comprises a vacuum tube comprising an anode 27 and a cathode 28 in which a filament 29, typically a tungsten wire wound helicoidally, is heated to a high temperature by means of an electric current. The beam of electrons 30 generated by the filament of the cathode 28 is accelerated to the anode 27, by means of acceleration voltage, not shown here. The beam of electrons 30 impacts the anode 27 at an emission focal point 31 of X-rays. In some embodiments, the anode is inclined at a given angle relative to the incident beam of electrons, for example 45°, given by way of non-limiting example.

The interaction between the incident beam of electrons 30 and the material making up the anode generates the X-rays. The beam of X-rays generated by the anode 27 from the emission focal point 31 of X-rays is omnidirectional. Part of this beam of X-rays then encounters the optic control device 10, which is configured to control the direction of said X-rays such that said X-rays of the beam $f_{i,j}$ at the output of the device 10 are substantially parallel to one another.

Substantially parallel means a beam whereof the rays are parallel to one another, or almost parallel to one another, due to optics failures of the device, as easily understood by a person skilled in the art.

In general, the source 2 comprises a protective casing (not shown) enclosing said source 2, and the optic device 10 is placed in said casing. In general, the optic device 10 is positioned near the anode 27, and in particular near the emission focal point 31 of X-rays. The optic device 10 is therefore positioned at the output of the anode 27 emitting the X-rays. It can be placed in the vacuum tube comprising the anode and the cathode or outside said tube. In another embodiment, the optic device 10 is positioned outside the protective casing of the source 2. Various embodiments of the optic device 10 are feasible.

Figure 5A:
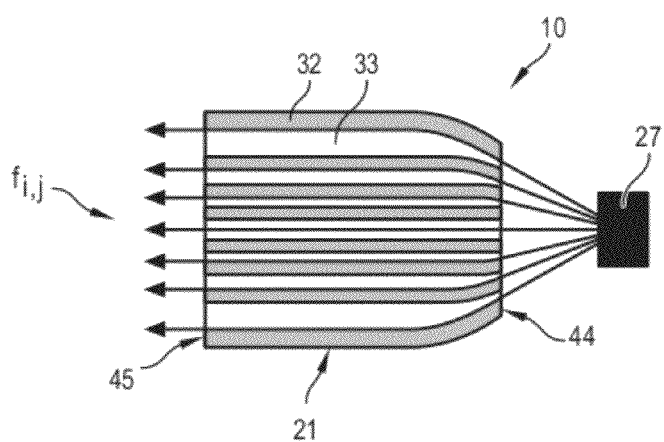
FIGS. 5A and 5B are a schematic representation of an optic device for controlling the direction of X-rays according to an exemplary embodiment of the present invention.
Figure 5B:
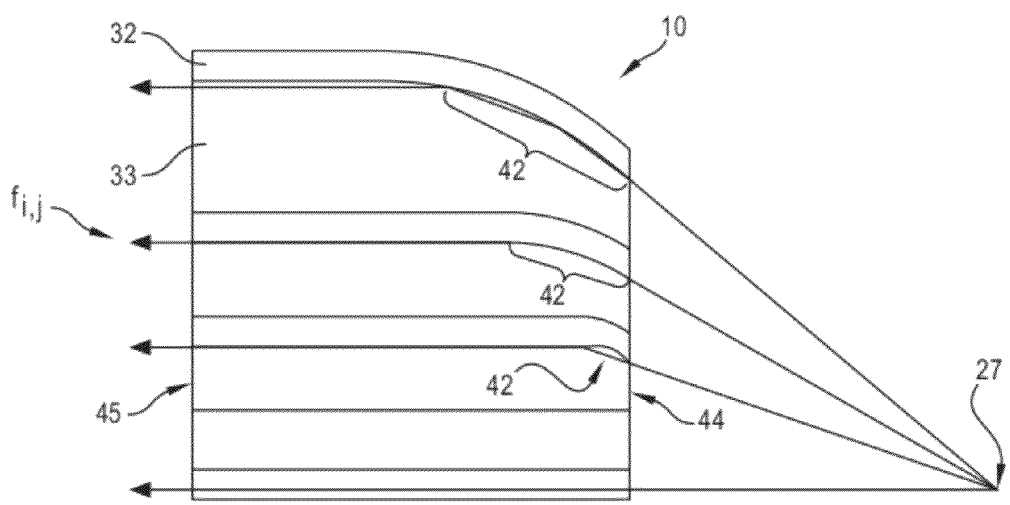

FIGS. 5A and 5B illustrate an exemplary embodiment of the optic device 10. As illustrated, the optic device 10 comprises a plurality of layers 21 of material. In particular, the optic device 10 is based here on the use of a succession of layers of material alternatively having high and low indices of refraction. Materials having a low refraction index are for example materials such as osmium, platinum or gold (inexhaustive list). Materials having a high refraction index are for example materials such as beryllium, hybrid lithium, magnesium (inexhaustive list).

The optic device 10 comprises at least one first sub-set 32 of layers presenting a refraction index belonging to a first interval of values and at least one second sub-set 33 of layers presenting a refraction index belonging to a second interval of values, the values of the first interval being greater than the values of the second interval (or inversely). In this case, the optic device 10 comprises a succession of layers belonging alternatively to the first sub-set 32 and to the second sub-set 33.

In one embodiment, the optic device 10 comprises successively alternating between a layer of a first material having a first refraction index and a layer of a second material having a second refraction index, the first index being greater than the second index (or inversely).

Alternating the refraction index of the layers of material making up the optic device 10 exploits the physical property of total reflection, that is an X-ray arriving at the interface between two materials of refraction index will be fully reflected, without refraction, if said ray has an angle of incidence less (or greater, according to the selected conventions) than a critical angle. Such an optic device 10 produces X-rays parallel at the outlet of said device, from a non-parallel beam of X-rays, for example conical in form.

In an exemplary embodiment, the optic device 10 comprises at least one first sub-set 32 of layers presenting a refraction index belonging to a first interval of values, at least a second sub-set 33 of layers presenting a refraction index belonging to a second interval of values, at least a third sub-set of layers presenting a refraction index belonging to a third interval of values, the values of the third interval being between the values of the second interval and of the first interval (or inversely), the device presenting a succession of layers belonging alternatively to the first sub-set 32, to the third sub-set and to the second sub-set 33. The exemplary embodiment provides interposing material of intermediate refraction index between material of high refraction index and material of low refraction index.

In an exemplary embodiment, an optic device 10 is used in which, apart from alternating of refraction indices, at least one sub-set of layers of the material has an incurved region 12 at the interface between said layers for redirection of incident X-rays into parallel X-rays. This is illustrated in FIG. 5B. The use of such regions increases the intensity of the beam of parallel X-rays at the outlet of the device 10.

Each incurved region 42 may have a curvature and/or a centre of curvature different from one layer to the other. Each incurved region 42 may be constituted by a plurality of joining segments, each segment presenting a radius of curvature. Each segment may have a constant radius of curvature. In the case of a straight segment, the radius of curvature is infinite. The radius of curvature of one segment can be different or identical to the radius of curvature of the other segments of the incurved region 12.

In an embodiment, the incurved region 42 is placed to the side of the inlet face 44 of X-rays in the optic device 10, while the interface between the layers is plane to the side of the outlet face 45 of the optic device 10. The region of layers whereof the interface is plane in fact plays the role of collimator.

In another embodiment, the incurved region 42 extends over the entire interface between the layers, from the inlet face 44 to the outlet face 45 of the device 10.

In an embodiment, the incurved region 42 extends from the inlet face to the outlet face 45 of the device 10 over a given length, with a given radius of curvature. The length of said region 42 is defined as the length producing, at the level of the outlet face 45 of the device 10, a tangent to the curve defined by said region which is horizontal, wherein horizontal means the axis of the central ray emitted by the anode, and which corresponds to a non-divergent ray.

The choice of materials, their thickness and the radius of curvature regulates the parallelism of X-rays at the outlet of the device (for example, a tolerance of 0.02° relative to the horizontal axis).

In an exemplary embodiment, the incurved region 42 extends from the inlet face to the outlet face 45 of the device 10 over a given length. The length of said region 42 now extends beyond the length to produce a tangent to the curve defined by said region which is horizontal. This embodiment produces rays with improved parallelism.

The optic device 10 can have several forms, according to need. It can be a stack of cylindrical layers, or polyhedral layers, i.e. parallelepiped. The layers of the device 10 may be adjacent to one another, without the presence of interstitial vacuum, or interstitial matter. The layers may be formed by conformal deposition.

As shown in FIG. 5B, the optic device 10 transforms a beam of X-rays having a generally conical form at the outlet of the anode 27 into a beam $f_{i,j}$ of X-rays having X-rays substantially parallel to one another.

In particular, the X-rays located on the periphery of the cone, and tending to diverge relative to the central rays, are reflected and redirected to the centre of the beam by means of layers 21 of material of the optic device 10, in particular the incurved regions 42. It is to be noted that this is a passive control of the direction of the rays Other embodiments of the device 10 are possible. It is known to use a multilayer optic device 10 which is curved as per a parabola. This technology is based on diffraction and not the total reflection, producing parallel X-rays (see for example US 2006/0018429).

Figure 6:
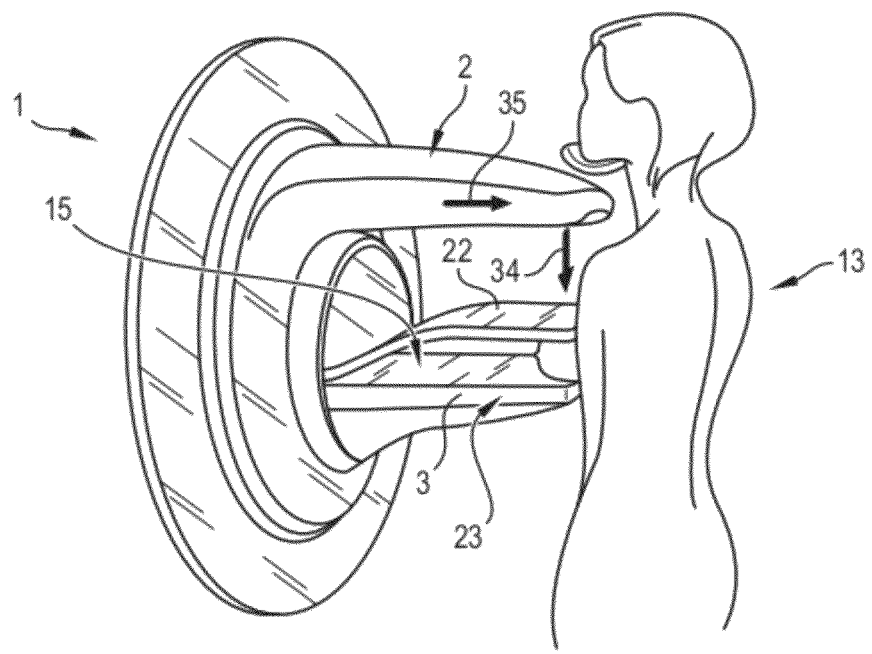
FIG. 6 is a schematic representation of a mammograph according to an exemplary embodiment of the present invention.

FIG. 6 is a schematic representation of a mammograph 1 according to an exemplary embodiment of the present invention. The source 2 and/or the detector 3 may be mobile. The source 2 can be shifted according to a first direction to increase or reduce the distance between the source 2 and the detector 3. This type of displacement is shown by the vertical arrow 34 in FIG. 6. It is clear that according to the relative position of the source 2 relative to the detector 3, this displacement will not always be vertical.

This displacement is for example done by means of a rail or via any other adapted displacement system known to the person skilled in the art. This displacement is for example controlled by a practitioner, via the control unit of the mammograph and the means of interaction of keyboard type. Alternatively, it is an automatic displacement piloted by the control unit of the mammograph.

The source 2 can be shifted according to a second direction, so as to increase or reduce the distance between the source 2 and the plane of the torso of the patient 12. This displacement is shown by arrow 35 in FIG. 6. It is understood that this displacement is not necessarily in the horizontal plane.

This displacement can be done in various ways, such as for example by translation of the source 2, or by a flap system of the source 2 or other. The source 2 can be shifted independently to the set formed by the detector 3 and the upper plate 22 serving as compression pad. The displacement can be done by any displacement system known to the person skilled in the art, such as a rail, a roller system, or other.

Displacement may be controlled by a practitioner, via the control unit of the mammograph and the means of interaction of keyboard type. Alternatively, it is an automatic displacement piloted by the control unit of the mammograph.

In an embodiment, the source 2 and the detector 3 can be shifted relatively in translation relative to one another. Translation is realizable along one or more axes belonging to the plane of the detector 3. The source 2 could then be moved, and/or the detector 3. This scans the detection surface 15 of the detector 3 with X-rays, and therefore takes an image of the whole breast placed on the detector 3.

These relative displacements are carried, out via any displacement system known to the person skilled in the art, and are applicable to the source 2 and/or to the detector 3.

Other displacements of the source 2 and/or of the detector 3 will be described hereinbelow.

The mammograph according to embodiments of the present invention produces one or more X-ray beams whereof the rays are parallel to one another. Consequently, it is possible to carry out relative nearing of the source 2 and of the detector 3, without the image of the breast being truncated, as would be the case with conical X-ray beams of the prior ar.

This produces a compact mammograph, in which the distance between the source 2 and the detector 3 is reduced. The distance between the detection surface 15 of the detector 3 and the emission focal spot of the source 2, from which the X-rays are emitted, is less than 70 cm, or 60 cm, or 50 cm, or 40 cm, or 30 cm, or 20 cm, or 10 cm. Other values are naturally feasible. It is clear that the distance between the emission focal spots of the X-rays of the source 2 and the detection surface of the detector 3 must stay above the thickness of the breast of the patient, to which the thickness of the compression pad must be added, but which can be negligible, of the order of a few millimeters, and this at least in the compressed position, such that the patient can position her breast between the lower block 23 and the compression pad 22.

In particular, contrary to devices of the prior art, it is possible to regulate the distance between the detection surface of the detector 3 and the emission focal spot so that said emission focal spot of X-rays of the source 2 is arranged in a zone located beneath the head 13 of the patient 12, along an axis orthogonal to the surface of the detector, generally vertical. Owing to the invention, this can be carried out without truncating the image of the breast. This is shown in FIG. 6 and is applicable irrespective of the size and dimensions of the patient.

For covering diverse patient morphologies, the distance between the detection surface of the detector 3 and the emission focal spot of the source 2 is between 5 cm and 30 cm, creating an emission focal spot of X-rays under the head of the patient, said distance being generally evaluated along an axis orthogonal to the detection surface of the detector, said axis being generally vertical. It is understood that any sub-interval of distance included in this interval is also included in the invention. In fact, the finest breasts generally have a thickness of the order of 2 cm in the compressed position, while the thickest breasts have a thickness of the order of tens of cm.

Also, the distance between the lower surface of the breast and the head of a woman, measured at the level of the chin of the woman, is taken for the quasi-totality of women between 20 and 30 cm. With the cited values, the emission focal spot of X-rays is therefore located in the zone located under the head of the patient.

The distance between the detection surface and the emission focal spot is generally evaluated according to the axis orthogonal to the detection surface of the detector 3. This distance could especially be regulated more precisely as a function of the effective distance between the lower face of the breast of the patient and the zone located under the head of the patient, at the level of the chin.

Embodiments of the present invention avoid the necessity of using a protective cover, which would serve to push back the head of the patient out of the imaging zone between the source and the detector.

In an exemplary embodiment, the source is adapted to emit a plurality of beams $f_{i,j}$ of X-rays. This can be done by using a plurality of cathodes, each cathode being capable of emitting a beam of electrons to one or more anodes. This creates a plurality of emission focal points of X-rays, and therefore a plurality of beams $f_{i,j}$ of X-rays, presenting rays parallel to one another.

The source 2 may be regulated so that the emission focal spot of the beams at the level of the anode is of a small size, for example of the order of a micron. In the case of emission of a plurality of beams $f_{i,j}$, it is possible to use a plurality of optic devices 10, located at the outlet of one or more anodes of the source 2, or alternatively a single optic device 10, controlling the direction of the X-rays, in such a way that said X-rays emitted by the source 2 to the detector 3 are substantially parallel to one another.

The source 2 may be adapted to emit a plurality of beams $f_{i,j}$ of X-rays from a plurality of emission focal points 31, said focal points 31 being arranged in a straight line. Therefore, in this case, this produces a source of one-dimensional type (cf. FIGS. 9A and 9B). Alternatively, the emission focal points 31 are arranged on a curve (not shown). Alternatively, the emission focal points 31 are arranged on a surface (cf. FIGS. 10A and 10B), thereby creating a bidimensional source 2.

In an embodiment, the source 2 and/or the detector 3 can be shifted relative to one another in different relative angular positions to take three-dimensional mammographic images by tomosynthesis. The relative angular displacement can for example consist of displacement of the source 2 on an arc of a circle, or on a line, or any other trajectory adapted to needs. This produces a series of images of the breast, corresponding to a series of projections of the breast according to different angles. In general, relative angular displacement has limited amplitude (between ±7° and ±60°, these values being given in a non-limiting way).

This set of images can be used to reconstruct a set of images which describe the volume of the breast by using image-processing algorithms known to the person skilled in the art. The image-processing algorithms for tomosynthesis especially include two large families which are non-iterative algorithms and iterative algorithms (examples of algorithms known to the person skilled in the art: "Filter Back Projection (FBP)", "Simultaneous Algebraic Reconstruction Technique (SART)").

Figure 7:
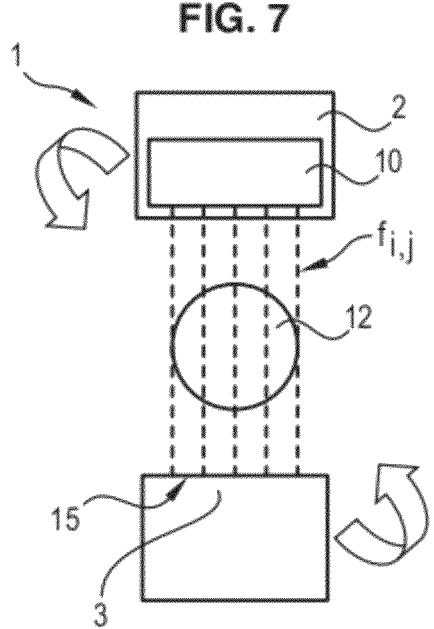
FIG. 7 is a representation of a mammograph according to an exemplary embodiment of the present invention.
Figure 8:
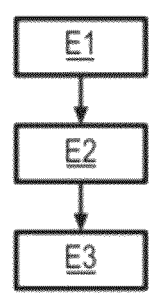
FIG. 8 is a schematic representation of steps of a process according to an exemplary embodiment of the present invention.

Embodiments of the present invention are also applicable to scanners dedicated to imaging of the breast. FIG. 7 schematically illustrates an example of such a mammograph.

In an exemplary embodiment, the source 2 and the detector 3 are capable of being set in rotation about the breast of the patient 12 according to an angle generally between 0 and 360°, or between 0 and 180°, or in a lesser angular interval of between 0 and 360°, for taking three-dimensional mammographic images, as in a scanner. The breast is seen in section in FIG. 7, and is therefore represented by a circle. The axis of rotation of the set comprising the source and the detector is generally the axis of symmetry of the breast passing through the nipple.

Different embodiments of the mammography process according to the invention will now be described, using one or the other of the embodiments of the mammograph described earlier.

In the first instance, the breast of the patient 12 is positioned on the lower block 23 comprising the detector 3, then compressed by the compression pad 22. The source 2 is previously moved away according to the second direction, as described earlier, so as to increase the distance between the source 2 and the plane of the torso of the patient 12, giving free access to the mammograph for the patient. This therefore pulls the source 2 back from the patient 12.

Once the breast of the patient 12 is in place, the source is moved again to the plane of the torso of the patient 12, for example by translation, to be positioned vis-à-vis the detector 3. The source 2 can also be shifted relative to the detector 3 according to the first direction, as described earlier, so as to increase or reduce the distance between the source 2 and the detector 3. The source 2 is generally located in a zone situated under the head 13 of the patient 12, according to a vertical axis, which is possible because of the device and process according to the invention.

Once the patient is in place, the process of taking mammographic images can start. The process comprises a step E1 consisting of emitting at least one beam of X-rays from the source 2 to the detector 3, the X-rays of the beam $f_{i,j}$ being substantially parallel to one another, due to the optic device 10 previously described. The beam $f_{i,j}$ of X-rays passes through the breast of the patient 12 and is collected by the detector 3, for taking mammographic images.

The process comprises a step E2 consisting of creating relative displacement between the source 2 and the detector 3, in such a way that the beam $f_{i,j}$ of X-rays emitted by the source 2 scans part or the entire detection surface 15 of the detector 3.

In general, the detection surface 15 comprises a set of detection elements. The beam $f_{i,j}$ of X-rays can be moved for example so as to scan each line of detection elements of the detection surface (so-called video scanning).

In an embodiment, the source 2 emits a plurality of beams $f_{i,j}$ of X-rays, and the process comprises a step E2 consisting of producing relative displacement between the source 2 and the detector 3, so as to scan part or all of the detection surface 15 by X-rays of the plurality of beams $f_{i,j}$.

Figure 9A:
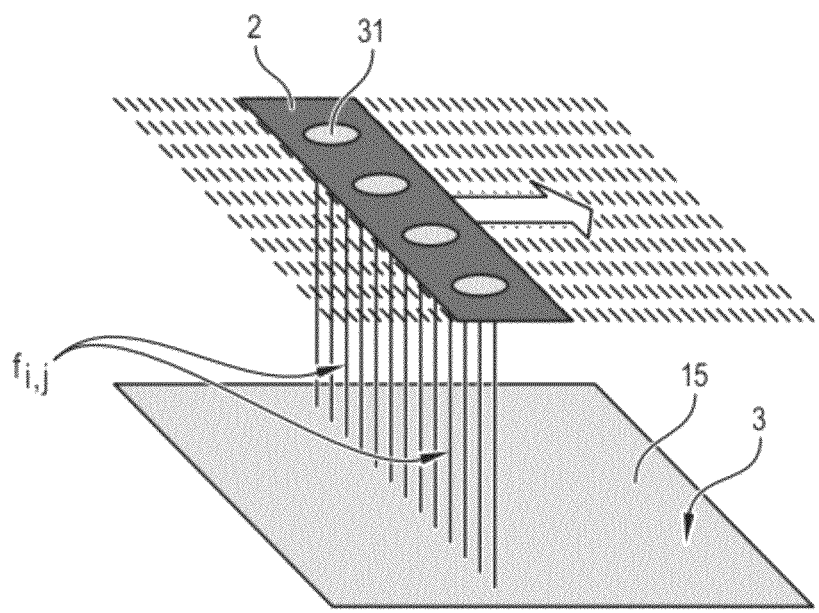
FIGS. 9A, 9B, 10A, 10B are schematic representations of sources and detectors according to an exemplary embodiment of the present invention.

In FIG. 9A, the source 2 emits a plurality of beams $f_{i,j}$, whereof the emission focal points 31 are located in a straight line (one-dimensional source). The source 2 is moved in translation relative to the detector 3 to scan the detection surface 15 of the detector 3.

Figure 9B:
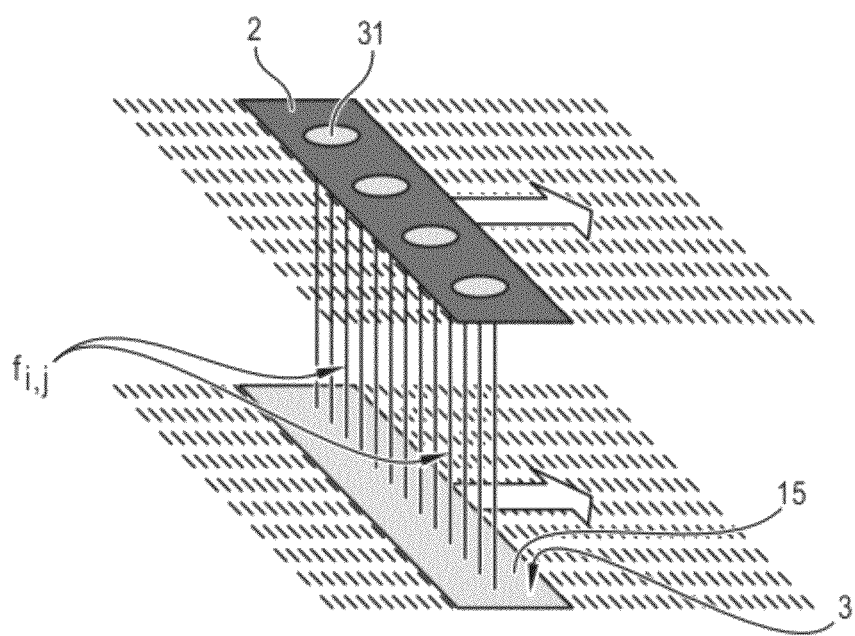

In FIG. 9B, the source emits a plurality of beams $f_{i,j}$, whereof the emission focal points 31 are located in a straight line (one-dimensional source).

Similarly, the detector 3 has a one-dimensional detection surface, that is, the detection elements are distributed mainly according to one axis. In order for a complete image of the breast of the patient to be taken, the source 2 and the detector 3 are moved conjointly, especially in translation.

In general, the process may comprise a step E3 consisting of successively emitting sub-sets of X-ray beams among the plurality of beams $f_{i,j}$ of X-rays of the source 2. Step E3 comprises: moving the detector 3 relative to the source 2, and successively emitting sub-sets of X-ray beams among the plurality of beams $f_{i,j}$ of X-rays of the source 2, said sub-sets of beams being selected to present X-rays directed to the detector 2 in displacement (that is to its detection surface 15).

Each sub-set of beams is emitted at an instant t, corresponding to the instant t when the X-rays of said sub-set of beams can reach the detection surface 15 of the detector 3 in movement.

This embodiment may limit the rise in temperature of the source 2 and its components (cathode, cathode filament, anode, etc.), since all the beams $f_{i,j}$ of X-rays are not emitted permanently. This improves the thermal balance of the source 2, and therefore its service life.

Figure 10A:
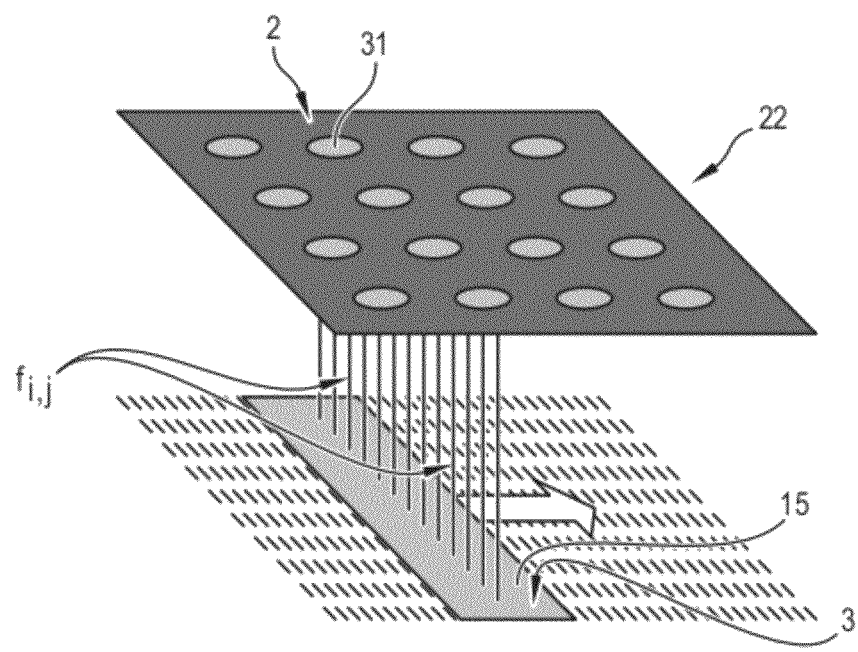

FIG. 10A illustrates a source 2 adapted to emit a plurality of beams $f_{i,j}$ from a plurality of emission focal points 31, said focal points 31 being arranged on a surface 22 (bidimensional source). The detector 3 includes a one-dimensional detection surface, whereof the pixels are distributed mainly according to one axis.

In this embodiment, it is advantageous to implement step E3 previously described.

In this embodiment, the detector 3 is moved in translation relative to the source 2 to produce an image of the whole breast, and different X-ray beams are successively emitted to the detector 3 in displacement, especially line by line.

Figure 10B:
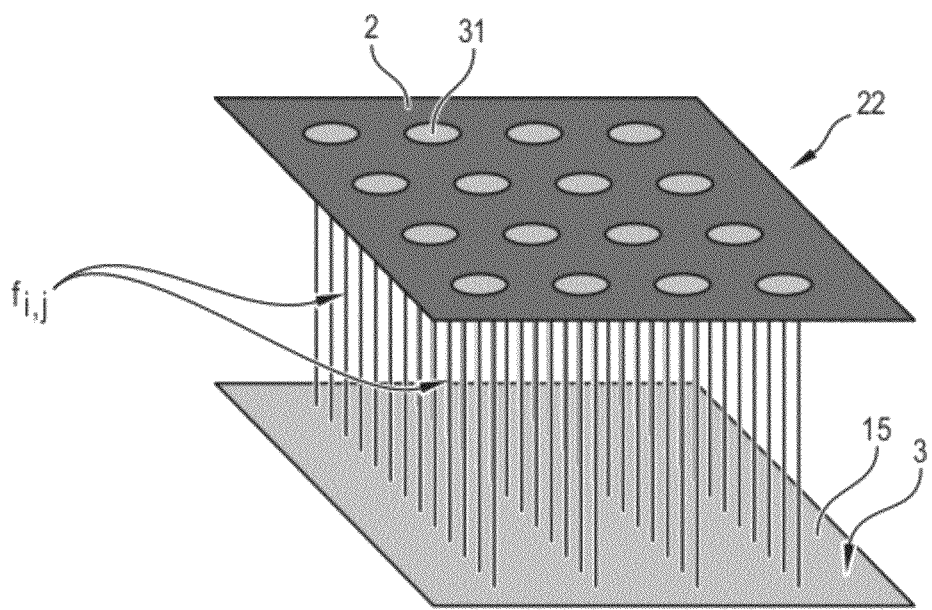

FIG. 10B illustrates an embodiment comprising a source 2 adapted to emit a plurality of beams $f_{i,j}$ from a plurality of emission focal points 31, said focal points 31 being arranged on one surface 22 (bidimensional source).

An embodiment has also been considered comprising a detector 3 having a bidimensional detection surface 15, that is, whereof the pixels are distributed over a set of successive lines. In this embodiment, it is clear that as a function of the space between the emission focal points 31 and the density of the X-ray beams, some detection elements of the detection surface 15 could not be reached by X-rays. It is therefore advantageous to carry out a step consisting of producing relative displacement between the source 2 and the detector 3 in such a way that the beams $f_{i,j}$ of X-rays emitted by the source 2 scan part or all of the detection surface 15 of the detector 3 so that all the detection elements of said surface can absorb X-rays emitted by the source and transmitted by the breast.

Other embodiments are feasible, according to the placement of the X-ray beams, their density, their number, the type of detection surface, the form of the detection surface, etc. The person skilled in the art will know how to adapt the embodiments which have just been described to the needs and applications of the mammograph.

In an embodiment of the mammography process the source 2 emits several X-ray beams each in a certain energy spectrum (and therefore frequency), each spectrum being different to the other spectra. A filter is positioned at the outlet of the source 2 and selects and filters the energy or the preferred energy range. This produces a succession of images obtained with X-rays of different energies. The mathematical processing of these images especially offers information on the composition of the breast (adipose, fibroglandular tissue, etc.), given that the different tissues have a different attenuation coefficient according to the energy of the incident X-rays.

Alternatively, or in addition, the detector 3 may play the role of energy filter of the X-rays. In this embodiment, the detector 3 is capable of detecting the energy or the range of energy of the X-rays emitted by the source 2 to the detector 3 for taking mammographic images at different emission energies of X-rays. This type of detector is generally based on photon-counting technology, comprising the capacity to discriminate between the energy of photons and the creation of an electric signal correlated to the energy of said photons.

As described previously, embodiments of the present invention is applicable to mammography by tomosynthesis. In this case, the source 2 and/or the detector 3 are moved relative to one another in different relative angular positions to take three-dimensional mammographic images by tomosynthesis. Relative angular displacement can, for example, consist of displacement of the source 2 on an arc of a circle, or on a line, or any other trajectory adapted to needs. This produces a series of images of the breast, corresponding to a series of projections of the breast according to different angles. In general, relative angular displacement has limited amplitude (between ±7° and ±60°, these values being given in a non-limiting manner).

This set of images can be used to reconstruct a set of images which describe the volume of the breast by using image-processing algorithms known to the person skilled in the art. The image-processing algorithms for tomosynthesis especially include two large families which are non-iterative algorithms and the iterative algorithms (examples of algorithms: "Filter Back Projection (FBP)", "Simultaneous Algebraic Reconstruction Technique (SART)").

The invention also applies to mammographs of scanner type, in which the source and the detector are set in rotation relative to the breast, at an angle generally between 0 and 360°.

As is evident, the invention has numerous advantages.

The mammograph obtained according to the invention is compact, with a distance between the source and the detector which can be reduced, due to use of parallel X-rays.

This compactness is advantageous, especially for positioning a mammograph in zones of reduced volume. For example, it is advantageous to arrange the mammograph according to the invention in a vehicle, for example of truck, bus, or other type, in order to access population zones which cannot or do not want to move to undergo mammographic examinations.

Accordingly, the invention also proposes a vehicle comprising a mammograph such as described. Advantageously, the mammograph is coupled to a teletransmission device for carrying out remote radiological interpretation in the case where the radiologist is located on a different site.

In addition, the invention proposes a mammograph reducing the risk of collision of a patient with the source of X-rays, given that the source can be located, under the head of the patient, without the image of the breast being truncated.

It is also noted that the invention facilitates and improves positioning of the breast of the patient in the mammograph, since no protective cover needs to be used, and since the detector can be moved, away from the plane of the torso of the patient during positioning.

Despite its compactness, the mammograph retains fine image quality and offers a high flow of rays, since they are controlled to be directed to the detector, in spite of the reduced distance between the source and the detector.

Another advantage of the invention is to enable reduction in thermal output of the source, especially in the case where sub-sets of X-ray beams are successively emitted, as described previously.

Finally, another advantage is that the invention also applies to mammographs for conducting tomosynthesis, and to mammographs of scanner type.

The invention therefore has numerous applications and has numerous advantages.

What is claimed is:

1. A mammograph comprising:
    a source of X-rays comprising a plurality of emission focal points arranged in a straight line, the source emitting X-ray beams parallel to one another;
    a detector of X-rays having a detection surface comprising a plurality of detection elements arranged in lines forming a bidimensional detection surface defining a plane, the source being configured to emit a plurality of X-ray beams to the detector;
    the source being movable relative to the detection surface so as to scan each line of the detection elements of the detection surface; and
    a distance between the emission focal points and the detection surface is regulated so that the source is positionable in a zone located under the head of a patient along an axis orthogonal to the detection surface.

2. The mammograph of claim 1, wherein a distance between the source and the detection surface is between about 5 cm and about 30 cm.

3. The mammograph of claim 1, wherein the source is configured to move so as to increase or reduce the distance between the source and the plane of the torso of a patient.

4. The mammograph of claim 1, further comprising an optic control device configured to control the direction of the X-rays emitted from the source such that the plurality of X-ray beams are substantially parallel one to the other.

5. The mammograph of claim 1, wherein the source and the detector can be shifted in rotation about the breast of the patient.

6. The mammograph of claim 1, wherein the detector is configured to detect the energy or a range of energy of X-rays emitted by the source to acquire mammographic images at different emission energies of X-rays.

7. The mammograph of claim 4 wherein the optic control device comprises a plurality of optic devices located near the outlet of the source of the X-ray.

8. A mammograph comprising:
    a source of X-rays comprising a plurality of emission focal points arranged in a bidimensional array defining a plane, the source emitting X-ray beams parallel to one another;
    a detector of X-rays having a detection surface comprising a plurality of detection elements arranged in lines forming a bidimensional detection surface defining a plane, the source being configured to emit a plurality of X-ray beams to the detector;
    the source being configured to move relative to the detection surface and emit X-rays from successive portions of the plurality of emission focal points so as to scan each line of the detection elements of the detection surface;
    a distance between the emission focal points and the detection surface is regulated so that the source is positionable in a zone located under the head of a patient, the distance between the source and the detection surface is between about 5 cm and about 30 cm; and
    the source and the detector can be shifted in rotation about the breast of the patient.

9. The mammograph of claim 8, further comprising an optic control device configured to control the direction of the X-rays emitted from the source such that the plurality of X-ray beams are substantially parallel one to the other.

10. The mammograph of claim 8, wherein the detector is configured to detect the energy or a range of energy of X-rays emitted by the source to acquire mammographic images at different emission energies of X-rays.

11. The mammograph of claim 9 wherein the optic control device comprises a plurality of optic devices located near the outlet of the source of the X-ray.

* * * * *